United States Patent [19]

Uenishi et al.

[11] Patent Number: 6,099,634
[45] Date of Patent: Aug. 8, 2000

[54] FAN- OR DISK-SHAPED TITANIUM OXIDE PARTICLES, PROCESSES FOR PRODUCTION THEREOF AND USES THEREOF

[75] Inventors: Toshiaki Uenishi; Takanori Yamasaki, both of Yamaguchi-ken, Japan

[73] Assignee: Titan Kogyo Kabushiki Kaisha, Yamaguchi-ken, Japan

[21] Appl. No.: 09/031,723

[22] Filed: Feb. 27, 1998

[30] Foreign Application Priority Data

Feb. 28, 1997 [JP] Japan ................................ 9-061840

[51] Int. Cl.$^7$ ................................................ C09C 1/36
[52] U.S. Cl. ......................... 106/436; 106/437; 106/438; 106/441; 106/442; 106/446; 423/610; 423/612; 423/615; 423/616; 424/59
[58] Field of Search .................................. 106/437, 438, 106/441, 442, 446; 423/610, 612, 615, 616; 424/59

[56] References Cited

U.S. PATENT DOCUMENTS 5,827,507 10/1998 Oshima et al. ............................ 424/59

FOREIGN PATENT DOCUMENTS

| 0 649 816 A1 | 4/1995 | European Pat. Off. ...... C01G 23/047 |
| 0 684 208 A1 | 11/1995 | European Pat. Off. ........ C01G 49/00 |
| 2 677 012 | 12/1992 | France .......................... C01G 23/047 |
| 55-154317 | 12/1980 | Japan .............................. C01G 23/05 |
| 62-003003 | 9/1987 | Japan .............................. C01B 13/14 |
| 07330338 | 12/1995 | Japan .............................. C01G 23/00 |

Primary Examiner—Mark L. Bell
Assistant Examiner—Michael J. DiVerdi
Attorney, Agent, or Firm—Pillsbury Madison & Sutro

[57] ABSTRACT

A titanyl sulfate solution or a titanium tetrachloride solution is neutralized with an alkali to form orthotitanic acid, to which hydrochloric acid is added such as to adjust the TiO$_2$ concentration to 80–140 g/L and the HCl concentration to 90–150 g/L and a synthesis reaction is performed at a temperature of 25–60° C. to produce titanium oxide particles in which needles aggregate and/or bind together to yield fan-shaped particles.

20 Claims, 3 Drawing Sheets

0.2 μm 0.2 μm 0.2 μm

FAN- OR DISK-SHAPED TITANIUM OXIDE PARTICLES, PROCESSES FOR PRODUCTION THEREOF AND USES THEREOF

BACKGROUND OF THE INVENTION

This invention relates to titanium oxide particles of specified shapes and processes for production thereof. More particularly, the invention relates to titanium oxide particles that are fan- or disk-shaped and which have a sufficiently high ultraviolet blocking effect (in particular, uv-A blocking effect) and high enough dispersibility and transparency to be useful as uv inhibitors in sunblock cosmetics, uv inhibiting paints, plastics and so forth. The invention also relates to processes for producing such titanium oxide particles.

Conventionally, ultrafine titanium oxide powders having a primary particle size of no more than 0.1 µm are commonly used in sunblock cosmetics, uv inhibiting paints, plastics and so forth with a view to providing an enhanced uv inhibiting effect.

However, ultrafine titanium oxide particles not larger than 0.1 µm are prone to agglomeration and producing a uniform dispersion of primary particles requires considerable effort and is sometimes impossible to accomplish.

Cosmetics incorporating ultrafine titanium oxide particles are effective in inhibiting uv-B (280–320 nm) but little effective in inhibiting uv-A (320–380 nm). If an increased amount of such titanium oxide particles is incorporated with a view to inhibiting uv-A, ease in use is inevitably compromised as exemplified by graininess and poor spreadability.

Thus, many problems are encountered in applying ultrafine titanium oxide particles to the purpose of blocking ultraviolet rays, particularly uv-A, and there has been a strong need to develop highly dispersible titanium oxide particles that have a high uv-A blocking effect and which are also transparent.

SUMMARY OF THE INVENTION

An object, therefore, of the present invention is to provide titanium oxides that have a sufficiently high ultraviolet blocking effect (in particular, uv-A blocking effect) and high dispersibility and transparency to be useful as uv inhibitors in sunblock cosmetics, uv inhibiting paints, plastics and so forth.

The present inventors conducted intensive studies in order to solve the aforementioned problems of the prior art and found that when orthotitanic acid resulting from alkali neutralization of a titanyl sulfate solution or a titanium tetrachloride solution was treated with hydrochloric acid under specified conditions, there was produced a rutile form of titanium oxide particles which were quite dissimilar in shape from the conventional titanium oxide particles. It was also found that the produced particles could easily be reduced to primary particles when dispersed in cosmetics, paints, plastics and so forth. The cosmetics, paints, plastics and the like which contained those particles turned out to be highly transparent and yet very effective in inhibiting ultraviolet rays, particularly, uv-A.

Thus, the present invention relates basically to fan-shaped titanium oxide particles which are needles aggregating and/or binding together and which have an edge length of 0.05–0.2 µm, preferably 0.05 to less than 0.2 µm, a thickness of 0.02–0.1 µm and a specific surface area of 90–180 m$^2$/g.

The fan-shaped titanium oxide particles having these characters are produced by a process comprising the steps of neutralizing a titanyl sulfate solution or a titanium tetrachloride solution with an alkali to form orthotitanic acid, adding hydrochloric acid to the orthotitanic acid such as to adjust the TiO$_2$ concentration to 80–140 g/L and the HCl concentration to 90–150 g/L, and performing a synthesis reaction at a temperature of 25–60° C.

The titanium oxide of the invention has transparency, is more effective in protecting from uv-A than the conventional types and can be easily reduced to primary particles in a dispersion medium; hence, it is useful as a uv inhibitor to be incorporated in sunblock cosmetics, uv inhibiting paints, plastics and so forth in order to achieve protection from uv radiations.

DESCRIPTION OF THE PREFERRED EMBODIMENTS

Figure 1:
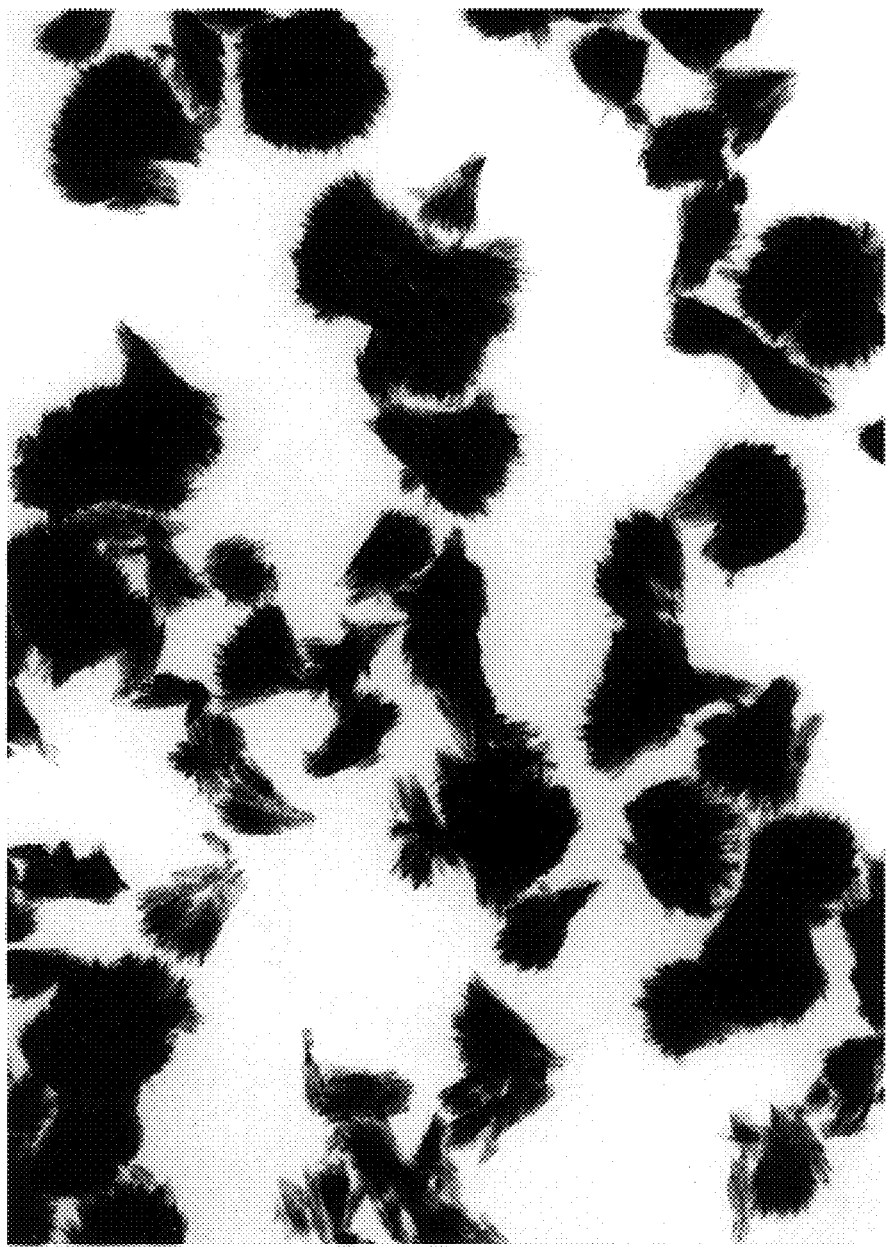
FIG. 1 is an electron photomicrograph (×100,000) of the fan-shaped titanium oxide particles produced in Example 2 of the invention.

The fan-shaped titanium oxide particles of the invention may be fired at a temperature not higher than 900° C. to produce disk-shaped titanium oxide particles having an edge length of 0.05–0.2 µm, preferably 0.05 to less than 0.2 µm a thickness of 0.01–0.1 µm and a specific surface area of 20–150 m$^2$/g.

In another preferred embodiment, the surfaces of the fan- or disk-shaped titanium oxide particles may be coated with a layer containing at least one element selected from among aluminum, silicon, titanium, zirconium and tin.

The fan- or disk-shaped titanium oxide particles of a coated type can be produced by a process comprising the steps of slurrying the titanium oxide particles produced by the aforementioned process and adding at least one water-soluble salt of aluminum, silicon, titanium, zirconium or tin to the slurry to neutralize same so that the surfaces of the titanium oxide particles are coated with a hydrous or non-hydrous oxide of said element.

The aforementioned fan-shaped or disk-shaped titanium oxide particle, with or without the top coating, may be incorporated in sunblock cosmetics, uv inhibiting paints or uv inhibiting plastic compositions.

The fan-shaped titanium oxide particles of the invention have an edge length of 0.05–0.2 µm, preferably 0.05 to less than 0.2 µm, a thickness of 0.02–0.1 µm and a specific surface area of 90–180 m$^2$/g. Desirably, they have an edge length of 0.08–0.15 µm, a thickness of 0.03–0.06 µm and a specific surface area of 95–130 m$^2$/g. If the edge length is smaller than 0.05 µm and the thickness is smaller than 0.02 µm and if the specific surface area is greater than 180 m$^2$/g, the fan-shaped titanium oxide particles are less effective in blocking uv light in the longer wavelength range. If the edge length and the thickness are greater than 0.2 µm and 0.1 µm, respectively, and if the specific surface area is smaller than 90 m$^2$/g, the fan-shaped titanium oxide particles are less transparent.

The fan-shaped titanium oxide particles of the invention are produced by a process comprising the steps of neutralizing a titanyl sulfate solution or a titanyl tetrachloride solution with an alkali to prepare orthotitanic acid, adding hydrochloric acid to the orthotitanic acid such as to adjust the $TiO_2$ concentration to 80–140 g/L, preferably 90–110 g/L, and the HCl concentration to 90–150 g/L, preferably 105–135 g/L, and performing a synthesis reaction at a temperature of 25–60° C., preferably 30–55° C.

The titanyl sulfate or titanium tetrachloride solution is preferably free from the iron content and this is in order to prevent the coloring of the finally obtained titanium oxide. Their neutralization with an alkali may be performed at room temperature. If the $TiO_2$ concentration during aging is lower than 80 g/L, the growth of particles is insufficient and only needles or rods will form that are conventionally used as uv inhibiting particles. The $TiO_2$ concentration during aging is preferably on the higher side; however, in view of the use of the fine particles of orthotitanic acid, thickening the aging mixture to a $TiO_2$ concentration in excess of 140 g/L requires a special apparatus and adds to the operating cost. If the HCl concentration is lower than 90 g/L, only needles or rods will form. If the HCl concentration exceeds 150 g/L, an anatase, rather than rutile, form of titanium oxide will occur. If the aging temperature is lower than 25° C., the reaction for the generation of rutile will not progress efficiently and an unduly prolonged time is necessary to bring the reaction to completeness. If the aging temperature exceeds 60° C., the desired titanium oxide particles cannot be produced.

The disk-shaped titanium oxide particles of the invention have an edge length of 0.05–0.2 μm, preferably 0.05 to less than 0.2 μm a thickness of 0.02–0.1 μm and a specific surface area of 20–150 $m^2/g$. Desirably, they have an edge length of 0.08–0.15 μm, a thickness of 0.03–0.06 μm and a specific surface area of 30–80 $m^2/g$. If the edge length is smaller than 0.05 μm, and the thickness is smaller than 0.02 μm and if the specific surface area is greater than 150 $m^2/g$, the disk-shaped titanium oxide particles are less effective in blocking uv light in the longer wavelength range. If the edge length and the thickness are greater than 0.2 μm and 0.1 μm, respectively, and if the specific surface area is smaller than 20 $m^2/g$, the disk-shaped titanium oxide particles are less transparent.

To produce the disk-shaped titanium oxide particles of the invention, the fan-shaped titanium oxide particles produced under the conditions set forth above may be fired at temperatures not higher than 900° C. Beyond 900° C., sintering occurs between particles to impair the dispersibility and transparency of the finally obtained particles.

The fan- or disk-shaped titanium oxide particles produced by the methods described above may have their surfaces coated with hydrous or non-hydrous oxides of metals such as aluminum, silicon, titanium, zirconium and tin in order to provide better stability in dispersion media and higher durability. The metal salts already mentioned above for use in preparing the coatings of said hydrous or non-hydrous oxides are not limited in any particular way. Even better dispersibility can be provided by treating the coatings of said hydrous or non-hydrous oxides of metals with silicone oil, various coupling agents or aliphatic acid compounds.

To reduce color-related problems such as segregation, mottles, color shades, white spots and bluing, skin-colored sunblock cosmetics conventionally use iron-containing titanium oxide which is produced by first coating the surfaces of $TiO_2$ particles with hydrous iron oxide and firing the particles to have iron dissolved in the crystals of titanium dioxide. The fan- or disk-shaped titanium oxide particles of the invention are suitable as basis material for the manufacture of said iron-containing titanium oxide.

EXAMPLES

The following examples are provided for the purpose of further illustrating the present invention but are in no way to be taken as limiting.

Example 1

A titanium tetrachloride solution was slowly dripped to 160 g/L of a sodium carbonate solution with care being taken to prevent the temperature of the mixture from exceeding 25° C. and the addition of the titanium tetrachloride was stopped when a pH of 10 was reached.

This neutralizing step produced a white precipitate of orthotitanic acid, which was filtered and thoroughly washed.

The thus obtained orthotitanic acid cake was repulped with dilute hydrohlcoric acid and, thereafter, conc. HCl was added to adjust the $TiO_2$ concentration to 90 g/L and the HCl concentration to 108 g/L.

Subsequently, the mixture was heated to 30° C. under stirring and left for 24 h at that temperature to synthesize a rutile form of titanium oxide.

To the resulting rutile-containing aqueous suspension, sodium aluminate was slowly added as 6% of $Al_2O_3$ under stirring which was continued for an additional hour to perform the $Al_2O_3$ treatment. Thereafter 400 g/L of sodium hydroxide was added to adjust the pH to 6.5 and the mixture was filtered, washed and dried to yield a rutile form of titanium oxide.

The rutile was composed of fan-shaped particles having an edge length of 0.09–0.15 μm, a thickness of 0.02–0.05 μm and a specific surface area of 166 $m^2/g$.

Example 2

Metatitanic acid prepared by hydrolysis in the sulfate process was digested with hot conc. sulfuric acid to produce a titanyl sulfate solution, which was slowly added to 160 g/L of a sodium carbonate solution with care being taken to prevent the temperature of the solution from exceeding 25° C. and the addition of the titanyl sulfate was stopped when a pH of 10 was reached.

This neutralizing step produced a white precipitate of orthotitanic acid, which was filtered and thoroughly washed.

The thus obtained orthotitanic acid cake was repulped with dilute hydrochloric acid and, thereafter, conc. HCl was added to adjust the $TiO_2$ concentration to 100 g/L and the HCl concentration to 120 g/L.

Subsequently, the mixture was heated at 50° C. under stirring and left for 12 h at that temperature to synthesize a rutile form of titanium oxide.

To the resulting rutile-containing aqueous suspension, sodium aluminate was slowly added as 6% of $Al_2O_3$ under stirring, which was continued for an additional hour to perform the $Al_2O_3$ treatment. Thereafter, 400 g/L of sodium hydroxide was added to adjust the pH to 6.5 and the mixture was filtered, washed and dried to yield a rutile form of titanium oxide.

The rutile was composed of fan-shaped particles having an edge length of 0.1–0.2 μm, a thickness of 0.02–0.1 μm and a specific surface area of 127 $m^2/g$. An electron photomicrograph of the $TiO_2$ particles is shown in FIG. 1.

Comparative Example 1

A reaction was performed as in Example 1 to synthesize a rutile form of titanium dioxide, except that the HCl concentration was adjusted to 160 g/L and the temperature of the mixture to 40° C. The actual product contained a minor amount of anatase.

Comparative Example 2

Figure 2:
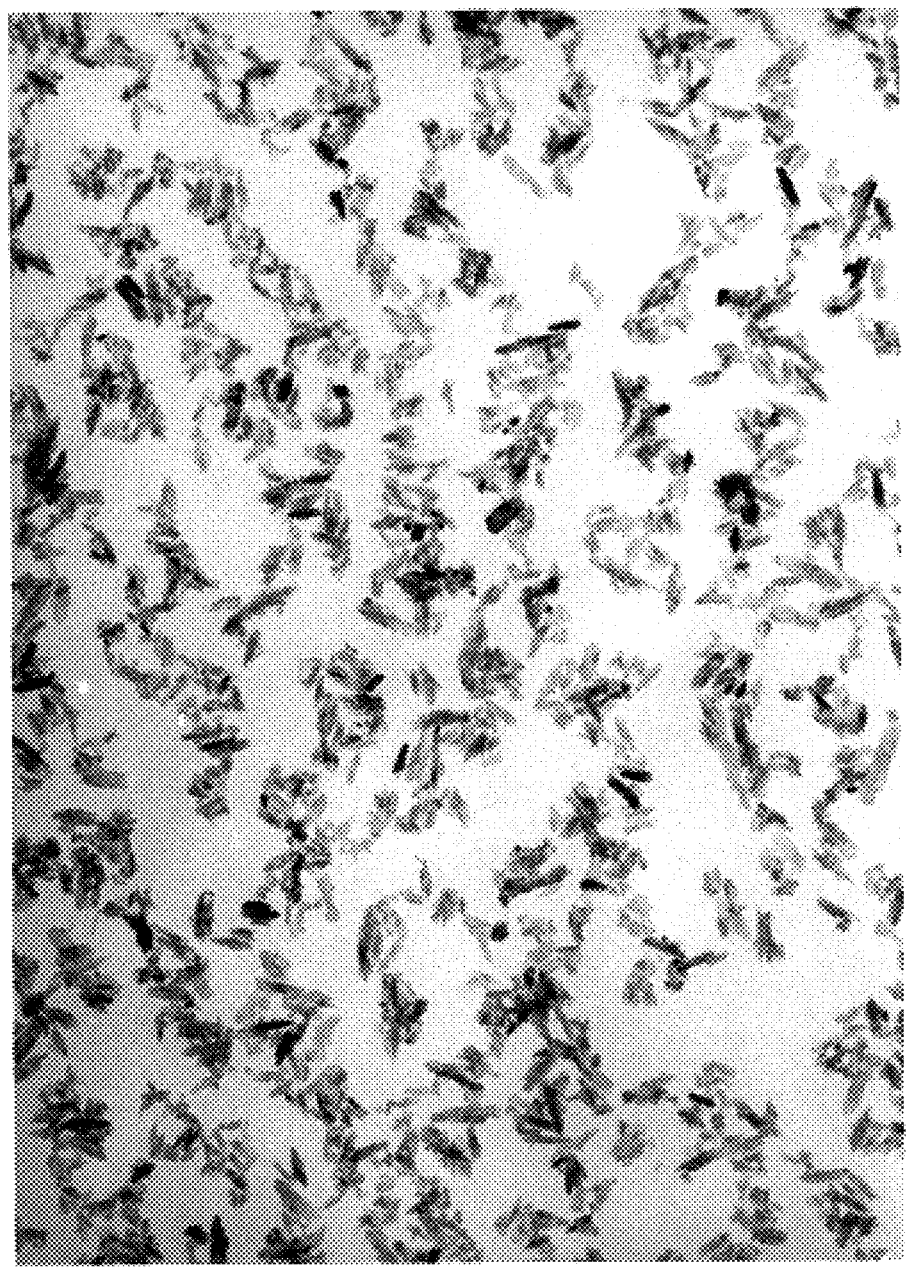
FIG. 2 is an electron photomicrograph (×100,000) of the rod-shaped fine titanium oxide particles produced in Comparative Example 2.
Figure 2:
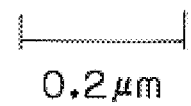

A reaction was performed as in Example 2 to a synthesize a rutile form of titanium oxide, except that the reaction temperature was the boiling point of the mixture. The rutile was composed of rod-shaped particles having a major axis of 0.03–0.12 μm, a minor axis of 0.01–0.02 μm and a specific surface area of 134 m²/g. An electron photomicrograph of the TiO₂ particles is shown in FIG. 2.

Example 3

Figure 3:
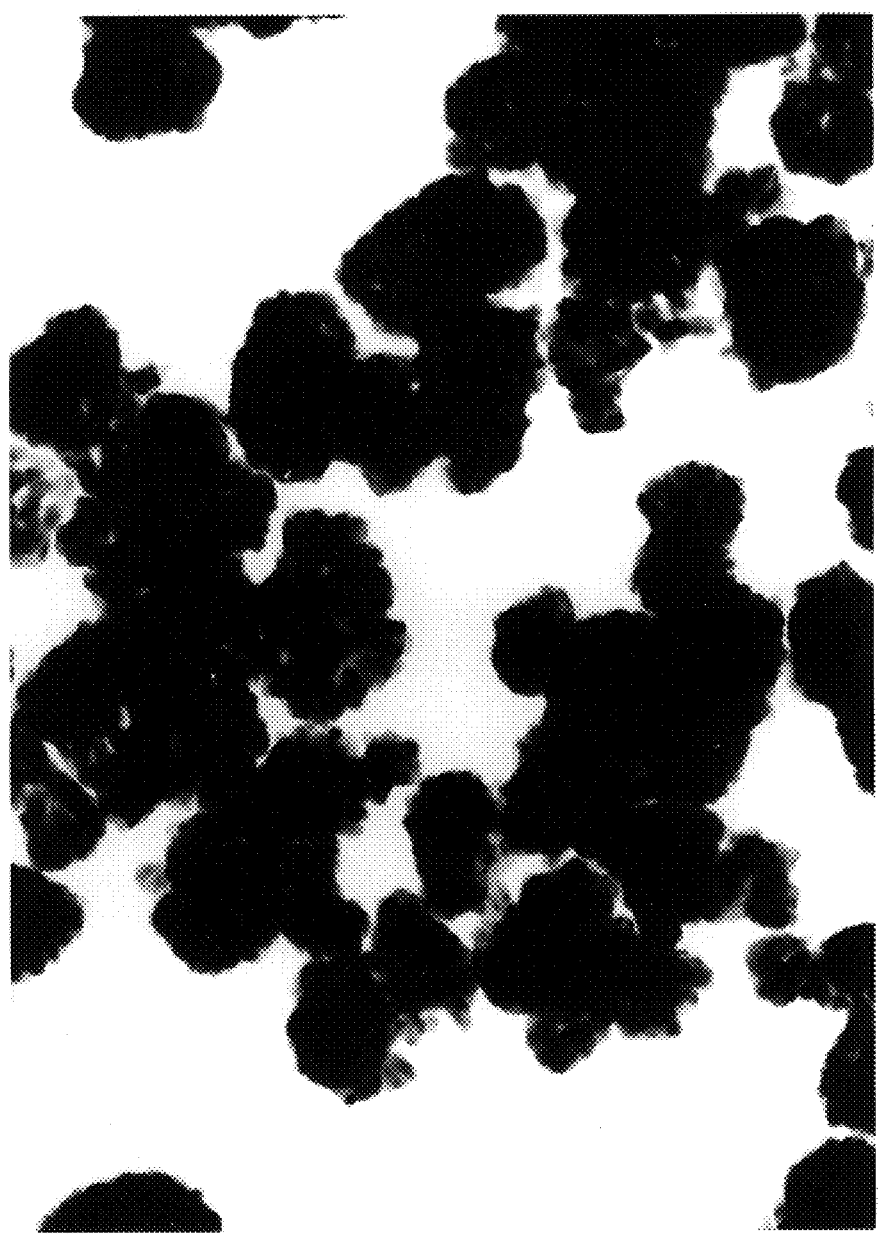
FIG. 3 is an electron photomicrograph (×100,000) of the disk-shaped titanium oxide particles produced in Example 3 of the invention.

The fan-shaped titanium oxide particles produced in Example 2 were fired at 700° C. for 30 min in a muffle furnace. The thus produced rutile was composed of disk-shaped particles having a diameter of 0.1–0.2 μm, a thickness of 0.02–0.1 μm and a specific surface area of 28 m²/g. An electron photomicrograph of the TiO₂ particles is shown in FIG. 3.

Test

A portion (0.42 g) of each of the rutiles produced in Examples 1–3 and Comparative Example 2, 7.2 g of an acrylic resin (ACRIDIC 47=712 of DAINIPPON INK & CHEMICALS, INC.), 1.5 g of melamine resin (Super Bekkamine L-117 of DAINIPPON INK & CHEMICALS, INC.), 10.5 g of a thinner (toluene/butyl acetate/S-100=3/5/2) and 100 g of 0.8-mm zircon beads were put into a 150-mL stoppered glass bottle and dispersed with a paint conditioner for 60 min to prepare a mill base.

To each of the prepared mill bases, 14.4 g of an acrylic resin and 3.0 g of a melamine resin were further added and mixed with a paint conditioner for 10 min; the resulting mixture was coated on a quartz glass plate by means of a 2-mil doctor blade.

The coatings were baked at 120° C. for 10 min and the transmittance of light through the coatings was measured at 300–800 nm with a spectrophotometer. The results are shown in Table below.

TABLE

| Run | Transmittance, % | | |
|---|---|---|---|
| | uv-B (300 nm) | uv-A (350 nm) | visible (550 nm) |
| Example 1 | 0 | 5 | 69 |
| Example 2 | 0 | 2 | 56 |
| Example 3 | 0 | 3 | 52 |
| Comparative Example 2 | 0 | 22 | 79 |

The above data show that the titanium oxide samples of Examples 1–3 were more effective in blocking uv-A than the comparative sample.

What is claimed is:

1. Fan-shaped titanium dioxide particles which are needles aggregating and/or binding together and which have an edge length of 0.05 to less than 0.2 μm, a thickness of 0.02–0.1 μm and a specific surface area of 90–180 m²/g.

2. Disk-shaped titanium dioxide particles which are produced by firing the fan-shaped titanium dioxide particles of claim 1 at a temperature no higher than 900° C. and which have an edge length of 0.05 to less than 0.2 μm, a thickness of 0.02–0.1 μm and a specific surface area of 20–150 m²/g.

3. The fan-shaped titanium dioxide particles according to claim 1, which have their surfaces coated with a layer containing at least one element of the group consisting of aluminum, silicon, titanium, zirconium and tin.

4. The disk-shaped titanium dioxide particles according to claim 2, which have their surfaces coated with a layer containing at least one element of the group consisting of aluminum, silicon, titanium, zirconium and tin.

5. A process for producing fan-shaped titanium dioxide particles which comprises the steps of neutralizing a titanyl sulfate solution or a titanium tetrachloride solution with an alkali to form orthotitanic acid, adding hydrochloric acid to the orthotitanic acid such as to adjust the TiO₂ concentration to 80–140 g/L and the HCl concentration to 90–150 g/L, and performing a synthesis reaction at a temperature of 25–60° C.

6. A process for producing disk-shaped titanium oxide particles by firing fan-shaped titanium oxide particles at a temperature not higher than 900° C., said fan-shaped titanium oxide particles being produced by the process of claim 5.

7. A process for producing fan-shaped titanium oxide particles, which comprising the steps of slurrying the fan-shaped titanium oxide particles produced by the process of claim 5 and adding at least one water-soluble salt of aluminum, silicon, titanium, zirconium or tin to the slurry to neutralize the same so that the surfaces of the titanium oxide particles are coated with a hydrous or non-hydrous oxide of said element.

8. A process for producing disk-shaped titanium oxide particles, which comprises the steps of slurrying the disk-shaped titanium oxide particles produced by claim 6 and adding at least one water-soluble salt of aluminum, silicon, titanium, zirconium or tin to the slurry to neutralize the same so that the surfaces of the titanium oxide particles are coated with a hydrous or non-hydrous oxide of said element.

9. A sunblock cosmetic incorporating the fan-shaped titanium oxide particles of claim 1.

10. A sunblock cosmetic incorporating the disk-shaped titanium oxide particles of claim 2.

11. A sunblock cosmetic incorporating the fan-shaped titanium oxide particles of claim 3.

12. A sunblock cosmetic incorporating the disk-shaped titanium oxide particles of claim 4.

13. A ultraviolet inhibiting paint incorporating the fan-shaped titanium oxide particles of claim 1.

14. A ultraviolet inhibiting paint incorporating the disk-shaped titanium oxide particles of claim 2.

15. A ultraviolet inhibiting paint incorporating the fan-shaped titanium oxide particles of claim 3.

16. A ultraviolet inhibiting paint incorporating the disk-shaped titanium oxide particles of claim 4.

17. A ultraviolet inhibiting plastic composition incorporating the fan-shaped titanium oxide particles of claim 1.

18. A ultraviolet inhibiting plastic composition incorporating the disk-shaped titanium oxide particles of claim 2.

19. A ultraviolet inhibiting plastic composition incorporating the fan-shaped titanium oxide particles of claim 3.

20. A ultraviolet inhibiting plastic composition incorporating the disk-shaped titanium oxide particles of claim 4.

* * * * *